United States Patent
Speckbacher et al.

(10) Patent No.: US 7,381,806 B2
(45) Date of Patent: Jun. 3, 2008

(54) CATIONIC AZO AZINE DYES AND COLORANTS THAT CONTAIN THESE COMPOUNDS

(75) Inventors: Markus Speckbacher, Aschaffenburg (DE); Hans-Jürgen Braun, Ueberstorf (CH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/516,886

(22) Filed: Sep. 7, 2006

(65) Prior Publication Data

US 2007/0073045 A1   Mar. 29, 2007

(30) Foreign Application Priority Data

Oct. 29, 2004   (DE)   ................... 102004052608.7
Jul. 11, 2005   (EP)   ................... PCT/EP05/07484

(51) Int. Cl.
  *C09B 56/18* (2006.01)
(52) U.S. Cl. ................. 534/604; 534/605; 534/615; 8/404; 8/405; 8/426; 8/917
(58) Field of Classification Search ................ 534/604, 534/605, 615; 8/404, 405, 426, 917
  See application file for complete search history.

(56) References Cited

U.S. PATENT DOCUMENTS 3,076,721 A    2/1963    Coles 4,910,152 A  *  3/1990   Meyers et al. ............... 436/501
2004/0187231 A1*  9/2004   Eliu et al. ....................... 8/405
2005/0000034 A1   1/2005   Eliu

FOREIGN PATENT DOCUMENTS

JP       58-49951     *   3/1983

OTHER PUBLICATIONS

International Search Report dated Nov. 24, 2005.
Y. Mori, *Chem. Pharm. Bull.*, 1981, 29(5), 1439-1442.

* cited by examiner

*Primary Examiner*—Fiona T Powers
(74) *Attorney, Agent, or Firm*—Idris N. McKelvey

(57) ABSTRACT

The objects of the present invention are novel cationic azo azine dyes of the generic formula (I),

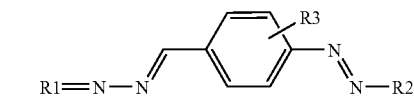

(I)

as well as colorants for keratin fibers that contain these compounds.

8 Claims, No Drawings

CATIONIC AZO AZINE DYES AND COLORANTS THAT CONTAIN THESE COMPOUNDS

The object of the present invention is new cationic azo azine dyes, as well as colorants that contain these compounds for use on fibers, in particular, keratin fibers, such as human hair.

As colorants for fiber materials, especially keratin-containing fibers, for example hair, wool, or fur, generally either direct-penetrating dyes or oxidative dyes produced by the oxidative coupling of one or more developer components with one or more coupler components are used. If needed, direct-penetrating dyes that are stable to oxidation by the oxidizing system can be added, in order to obtain special coloring effects. Direct-penetrating dyes are incorporated into suitable vehicles, and then applied to the fiber. This process, generally known as tinting, is easy to perform, remarkably mild, and is characterized by minimal damage to the keratin fiber if no ammonia or peroxide is added. Nevertheless, the dyes used here must fulfill several requirements. They must be quite safe from a toxicological and dermatological perspective and they must enable the achievement of coloring that has the desired intensity and brilliance. Moreover, the coloring obtained must have good lightfastness, resistance to shampooing, and conditioners, as well as good resistance to rubbing.

As a rule, a direct-penetrating, nonoxidative colorant for keratin fibers requires a combination of different nonoxidative dyes in order to achieve a certain tinting. Since the array of dyes that can adequately fulfill the stated requirements is limited, there is a significant need for additional dyes of this type.

The goal of the present invention is to provide direct-penetrating dyes that satisfy these requirements for the coloring of keratin fibers, especially of human hair.

Surprisingly, it has been found that cationic azo azine dyes of the generic formula (I) can be used as direct-penetrating dyes in coloring preparations without added oxidizing agents and can be applied to keratin fibers under mild conditions.

The objects of the present invention are thus cationic dyes of the generic formula (I),

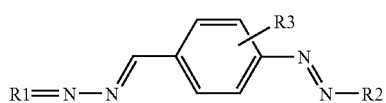

where

R1 is selected from residues having the formulas (II), (III), (IV), (V), and (VI),

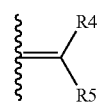

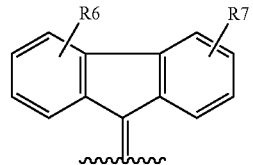

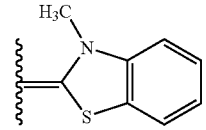

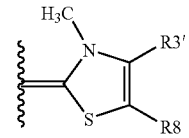

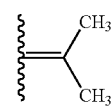

R2, R4, and R5 can be the same or different and independently from one another are selected from residues having the formulas (VII), (VIII), and (IX);

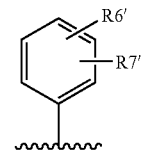

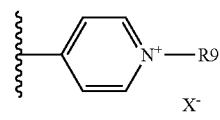

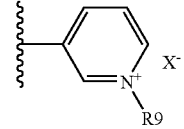

R3, R3', R6, R6', R7, R7', and R8 can be the same or different and independently from one another can equal hydrogen, a $C_1$-$C_6$-alkylamino group, a $C_1$-$C_6$-N,N-dialkylamino group, a $C_1$-$C_6$-N,N-dihydroxyalkylamino group, a $C_1$-$C_6$-N-hydroxyalkyl-N-alkylamino group, a $C_1$-$C_6$-alkylcyano group, a nitro group, a cyano group, an amino group, a nitroso group, a hydroxyl group, a methoxymethyl group, a tert-butyl group, an iso-propyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C_1$-$C_6$-alkylcarboxylic acid ester group, a $C_1$-$C_6$-alkylsulfonic acid group, a $C_1$-$C_6$- alkylsulfonic acid ester group, or an -N-(L)-B⁺-group; L represents a $C_1$-$C_6$ alkylene group and B⁺ represents a) an aromatic, heterocyclic quaternary ammonium compound, preferably a quaternary compound of N-methylimidazole, N-allylimidazole, 2-ethylimidazole or 1,2-dimethylimidazole or a quaternary compound of pyridine, 4-dimethylaminopyridine, pyrimidine, pyrazole, N-methylpyrazole or quinoline; or b) a nonaromatic heterocyclic quaternary ammonium compound, especially a quaternary compound of N-methylmorpholine, N-ethylmorpholine, 1-methylpiperidine; or c) a quaternary alkylammonium compound or arylammonium compound of the formula $NR_aR_bR_c$, where $R_a$, $R_b$, and $R_c$ independently from one another can indicate a benzyl residue, a phenyl residue or a $C_1$-$C_6$-alkyl residue, especially a methyl residue, an ethyl residue, a propyl residue, an isopropyl residue or a butyl residue, where the aforementioned alkyl group can be unsubstituted or substituted with one or more hydroxyl groups or amino groups; or d) a quaternary phosphonium group, for example a tributylphosphonium group, and especially a trimethylammonium group or a triethylammonium group; R9 equals a branched or linear $C_1$-$C_6$-alkyl group, a branched or linear $C_2$-$C_4$-hydroxyalkyl group or a branched or linear $C_4$-$C_6$-polyhydroxyalkyl group; and X⁻ is an anion, for example a sulfate anion, a phosphate anion, a hydrogen phosphate anion, an oxalate anion, a formate anion, an acetate anion, a citrate anion, a tartrate anion, a malonate anion, a pyruvate anion or an iodide anion, where chloride ion, bromide ion and methyl sulfate anion are especially preferred; and where at least one of the residues R1, R2, and R3 exhibits at least one cationic group.

Examples of suitable cationic direct-penetrating dyes of the generic formula (I) that can be named include:

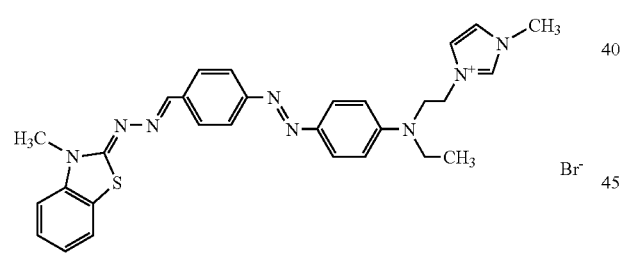

3-(2-{ethyl-4-[(E)-(4-{(E)-[(2Z)-2-(3-methyl-1,3-benzothiazol-2(3H)ylidene)hydrazono]methyl}-phenyl)-diazenyl]anilino}ethyl)-1-methyl-1H-imidazol-3-ium bromide

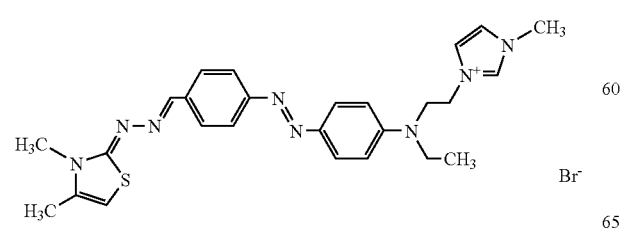

3-{2-[4-[(E)-(4-{(E)-[(2Z)-2-(3,4-dimethyl-1,3-thiazol-2(3H)ylidene)hydrazono]methyl}phenyl)-diazenyl](ethyl)anilino]ethyl}-1-methyl-1H-imidazol-3-ium bromide

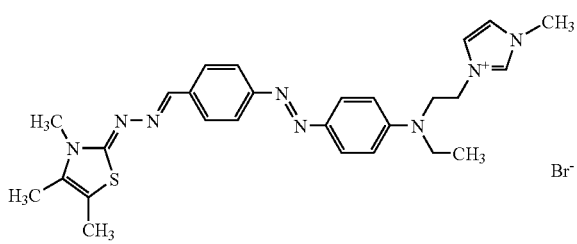

3-(2-{ethyl-4-[(E)-(4-{(E)-[(2Z)-2-(3,4,5-trimethyl-1,3-thiazol-2(3H)ylidene)hydrazono]methyl}-phenyl) diazenyl]anilino}ethyl)-1-methyl-1H-imidazol-3-ium bromide

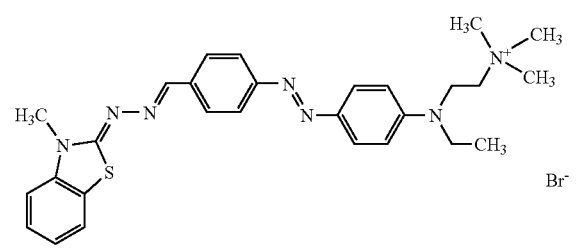

2-{ethyl-4-[(E)-(4-{(E)-[(2Z)-2-(3-methyl-1,3-benzothiazol-2(3H)ylidene)hydrazono]methyl}-phenyl) diazenyl]anilino}-N,N,N-trimethylethanaminium bromide

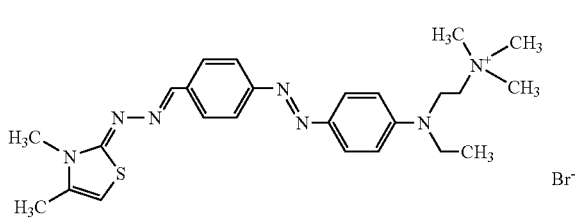

2-[4-[(E)-(4-{(E)-[(2Z)-2-(3,4-dimethyl-1,3-thiazol-2(3H)ylidene)hydrazono]methyl}phenyl)-diazenyl](ethyl)anilino]-N,N,N-trimethylethanaminium bromide

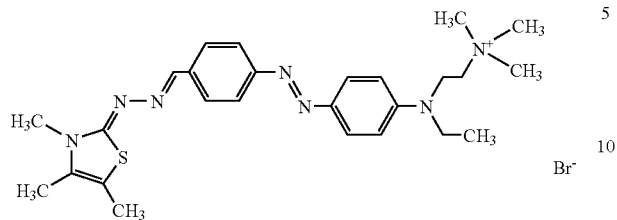

2-{ethyl-4-[(E)-(4-{(E)-[(2Z)-2-(3,4,5-trimethyl-1,3-thiazol-2(3H)ylidene) hydrazono methyl}-phenyl) diazenyl]anilino}-N,N,N-trimethylethanaminium bromide

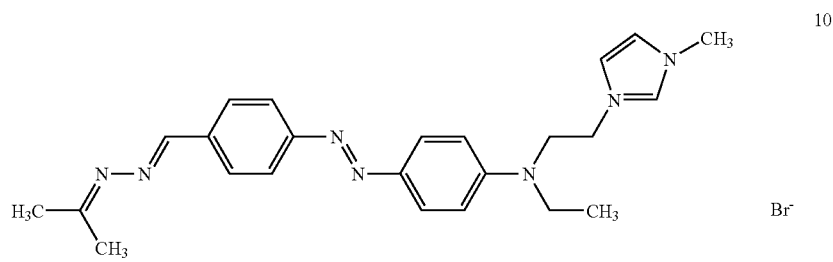

3-(2-{ethyl-4-[(E)-(4-{(E)-[(1-methylethylidene) hydrazono]methyl}phenyl)diazenyl]anilino}ethyl)-1-methyl-1H-imidazol-3-ium bromide

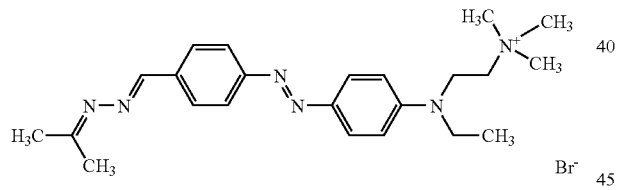

2-{ethyl-4-[(E)-(4-{(E)-[(1-methylethylidene)hydrazono]methyl}phenyl)diazenyl]anilino}-N,N,N-trimethylethanaminium bromide

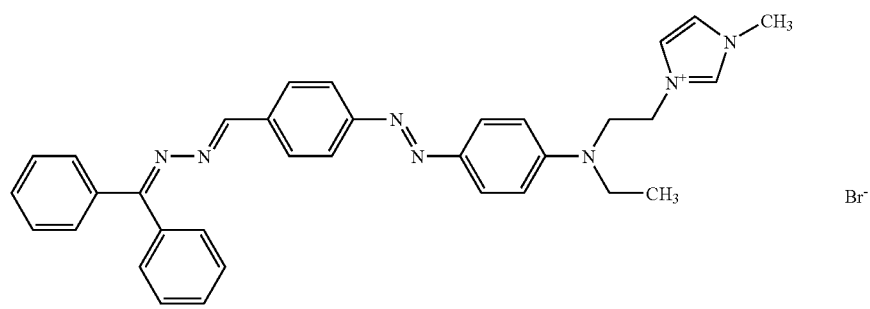

3-{2-[(E)-(4-{(E)-[(diphenylmethylidene)hydra-
zono]methyl}phenyl)diazenyl](ethyl)anilino]ethyl}-
1-methyl-1H-imidazol-3-ium bromide

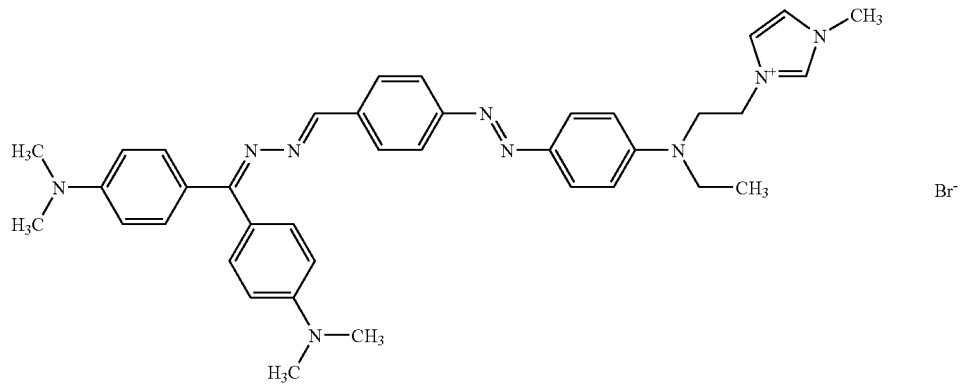

3-{2-[4-((E)-{4-[(E)-({bis-[4-(dimethylamino)phe-
nyl]methylidene}hydrazono)methyl]
phenyl}diazenyl)(ethyl)anilino]ethyl}-1-methyl-1H-
imidazol-3-ium bromide

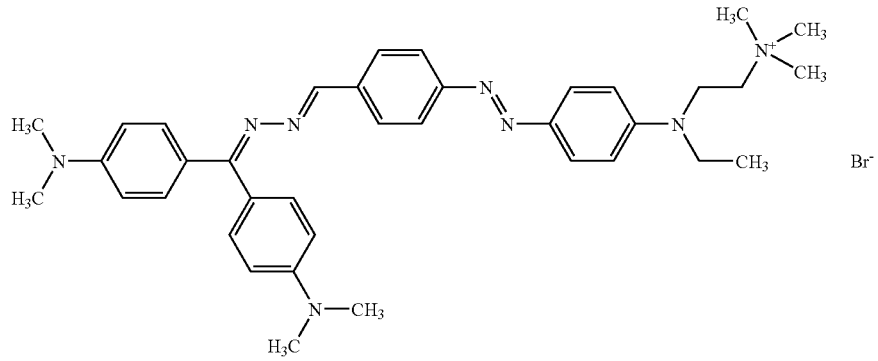

2-[4-((E)-{4-[(E)-({bis-[4-(dimethylamino)phenyl]
methylidene}hydrazono)methyl]phenyl}diazenyl)
(ethyl)anilino]-N,N,N-trimethylethanaminium bro-
mide

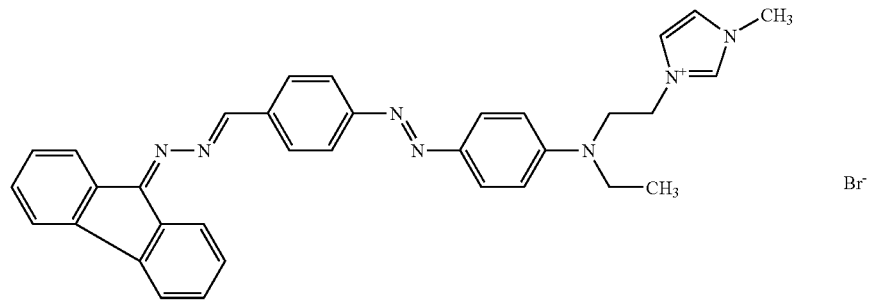

3-{2-[ethyl-4-((E)-{4-[(E)-(9H-fluoren-9-ylidenehydrazono)methyl]phenyl}diazenyl)anilino]ethyl}-1-methyl-1H-imidazol-3-ium bromide
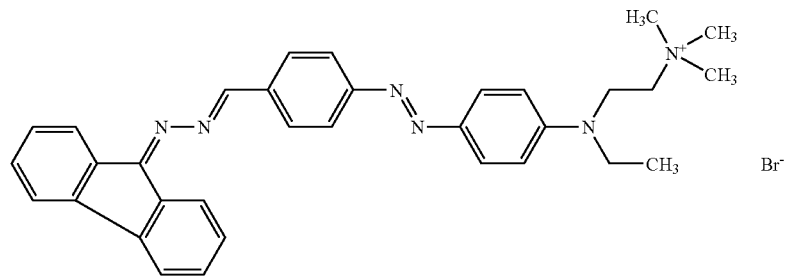
2-[ethyl-4-((E)-{4-[(E)-(9H-fluoren-9-ylidenehydrazono)methyl]phenyl}diazenyl) anilino]-N,N,N-trimethylethanaminium bromide
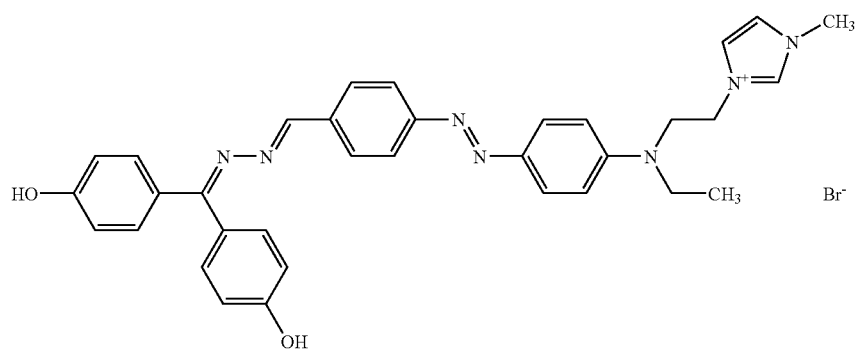
3-{2-[4-{(E)-[4-((E)-{[bis-(4-hydroxyphenyl)methylidene]hydrazono}methyl)phenyl]diazenyl}(ethyl)anilino]ethyl}-1-methyl-1H-imidazol-3-ium bromide
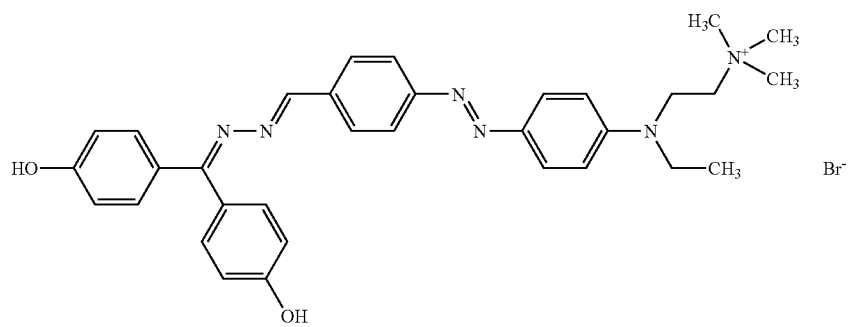

2-[4-{(E)-[4-((E)-{[bis-(4-hydroxyphenyl)methylidene]hydrazono}methyl)phenyl]diazenyl}(ethyl)anilino]-N,N,N-trimethylethanaminium bromide

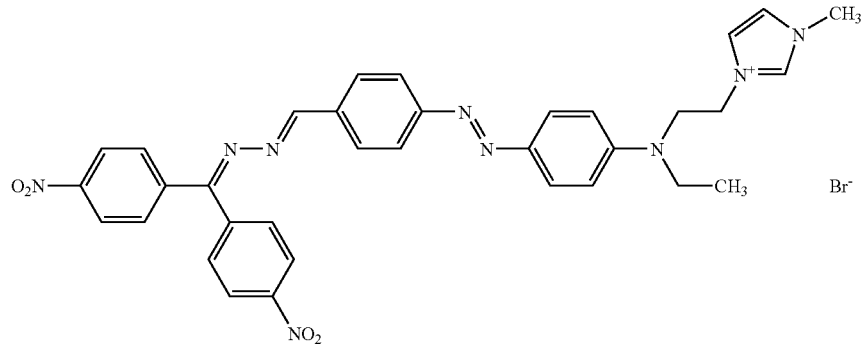

3-{2-[4-{(E)-[4-((E)-{[bis-(4-nitrophenyl)methylidene]hydrazono}methyl)phenyl]diazenyl}(ethyl)anilino]ethyl}-1-methyl-1H-imidazol-3-ium bromide

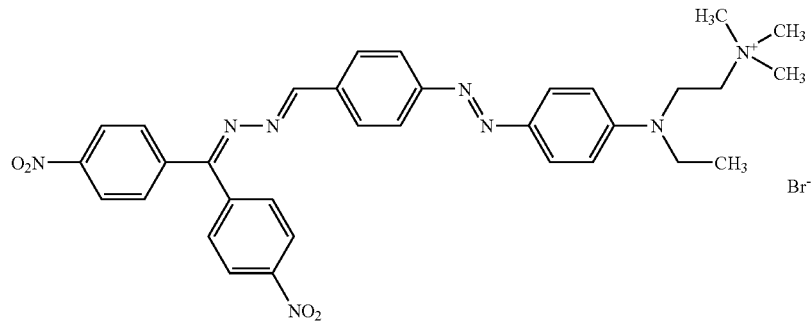

2-[4-{(E)-[4-((E)-{[bis-(4-nitrophenyl)methylidene]hydrazono}methyl)phenyl]diazenyl}(ethyl)anilino]-N,N,N-trimethylethanaminium bromide 4-[(Z)-[(2E)-2-(4-{(E)-[4-(dimethylamino)phenyl]diazenyl}benzylidene)hydrazono](phenyl)methyl]-1-methylpyridinium methyl sulfate

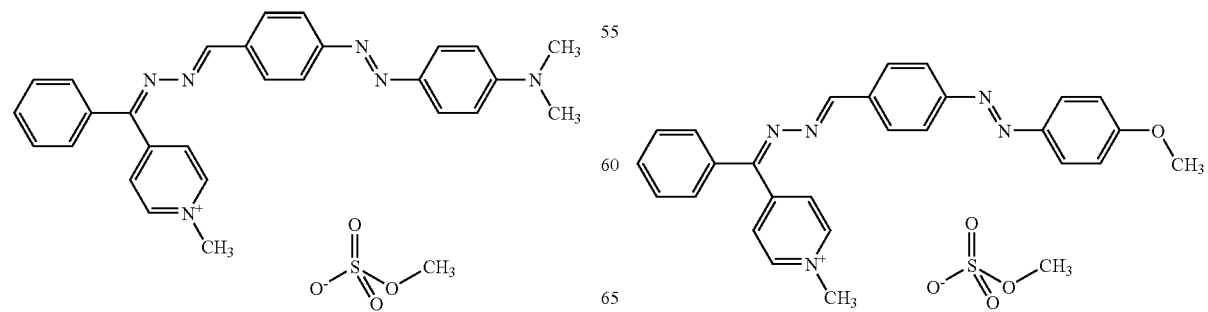

4-[(Z)-((2E)-2-{4-[(E)-(4-methoxyphenyl)diazenyl]benzylidene}hydrazono)(phenyl) methyl]-1-methylpyridinium methyl sulfate; and

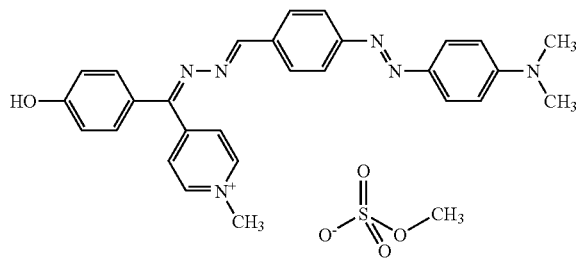

4-[(Z)-[(2E)-2-(4-{(E)-[4-(dimethylamino)phenyl]diazenyl}benzylidene)hydrazono](4-hydroxy-phenyl)methyl]-1-methylpyridinium methyl sulfate.

Preferred compounds of the generic formula (I) are: 3-(2-{ethyl-4-[(E)-(4-{(E)-[(2Z)-2-(3-methyl-1,3-benzothiazol-2(3H)ylidene)hydrazono]methyl}phenyl)diazenyl]anilino}ethyl)-1-methyl-1H-imidazol-3-ium bromide; 3-{2-[4-[(E)-(4-{(E)-[(2Z)-2-(3,4-dimethyl-1,3-thiazol-2-(3H)ylidene)hydrazono]methyl}phenyl)diazenyl](ethyl)anilino]ethyl}-1-methyl-1H-imidazol-3-ium bromide; 3-(2-{ethyl-4-[(E)-(4-{(E)-[(2Z)-2-(3,4,5-trimethyl-1,3-thiazol-2(3H)ylidene)hydrazono]methyl}phenyl)diazenyl]anilino}ethyl)-1-methyl-1H-imidazol-3-ium bromide; 2-{ethyl-4-[(E)-(4-{(E)-[(2Z)-2-(3-methyl-1,3-benzothiazol-2(3H)ylidene)hydrazono]methyl}phenyl)diazenyl]anilino}-N,N,N-trimethylethanaminium bromide; 2-[4-[(E)-(4-{(E)-[(2Z)-2-(3,4-dimethyl-1,3-thiazol-2(3H)ylidene)hydrazono]methyl}phenyl)diazenyl](ethyl)anilino]-N,N,N-trimethylethanaminium bromide; 2-{ethyl-4-[(E)-(4-{(E)-[(2Z)-2-(3,4,5-trimethyl-1,3-thiazol-2(3H)ylidene)-hydrazono]methyl}phenyl)diazenyl]anilino}-N,N,N-trimethylethanaminium bromide; 3-{2-[4-((E)-{4-[(E)-({bis-[4-(dimethylamino)phenyl]methylidene}hydrazono)methyl]phenyl}diazenyl)-(ethyl)anilino]ethyl}-1-methyl-1H-imidazol-3-ium bromide and 3-{2-[ethyl-4-((E)-{4-[(E)-(9H-fluoren-9-ylidenehydrazono)methyl]phenyl}diazenyl)anilino]ethyl}-1-methyl-1H-imidazol-3-ium bromide.

The dye derivatives of the present invention of the generic formula (I) are accessible through standard operations from commercially available or easily prepared components.

The general procedure by Y. Mori (*Chem. Pharm. Bull.* 1981, 29 (5), 1439-1442) can be used to prepare azo dyes with formyl substituents in the para-position. The condensation of these azo dyes with various hydrazone components in an acetic acid medium provides the corresponding azo azine dyes in good yield. A representative synthesis pathway is shown in Diagram 1.

Diagram 1:

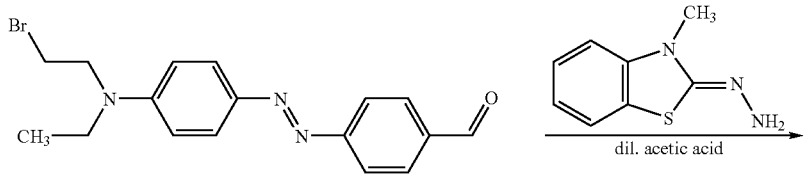

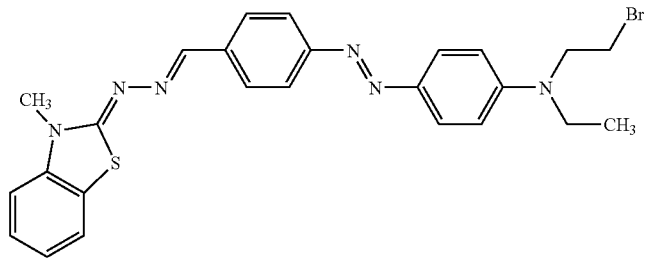

The cationic dye is obtained in the final step via substitution of a suitable leaving group with an N-nucleophile (e.g., N-methylimidazole) in a dipolar aprotic solvent (e.g., acetonitrile) (Diagram 2).

Diagram 2:

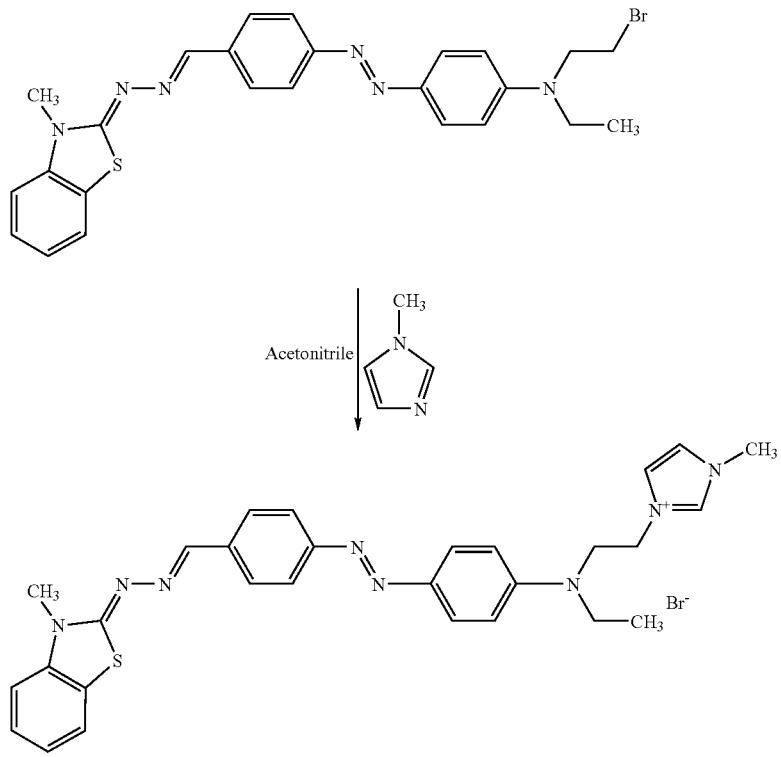

The cationic azo azine dye of the present invention of the generic formula (I) enables a uniform coloring of fiber materials, especially human hair, with good stability to light, sweat, and shampooing. The compounds of the present invention of the generic formula (I) exhibit intense, brilliant coloring of keratin fibers, especially of human hair, but also wool, fur, or other fiber materials, under mild conditions.

A further object of the present invention is an agent for the coloring of keratin fibers, especially human hair, which contains at least one derivative of the generic formula (I).

A colorant of the present invention contains cationic azo azine dyes of the generic formula (I) preferably in an amount of from 0.01 to 10 percent by weight, and particularly from 0.1 to 8 percent by weight.

In addition to dyes of the generic formula (I), a colorant of the present invention can also contain further known direct dyes from the group that includes nitro dyes, azo dyes, athraquinone dyes, triphenylmethane dyes and basic or acidic dyes, individually or in mixtures with each other, such as for example 1,4-bis-[(2-hydroxyethyl)amino]-2-nitrobenzene, 1-(2-hydroxyethyl)amino-2-nitro-4-[di-(2-hydroxyethyl)amino]benzene, (HC Blue No. 2), 1-amino-3-methyl-4-[(2-hydroxyethyl)amino]-6-nitrobenzene, (HC Violet No. 1), 4-[ethyl-(2-hydroxyethyl)amino]-1-[(2-hydroxyethyl)amino]-2-nitrobenzene hydrochloride (HC Blue No. 12), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di-(2-hydroxyethyl)amino]-2-nitrobenzene, (HC Violet No. 2); 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di-(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl) amino]-2-nitrobenzene (HC Red No. 3), 4-amino-2-nitro-1-((prop-2-en-1-yl)amino)benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene, (HC Orange No. 3), 1-amino-5-chloro-4-[(2,3-dihydroxypropyl)amino]-2-nitrobenzene (HC Red No. 10), 5-chloro-1,4-[di-(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 3-amino-6-(methylamino)-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene, (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No.9), 1-[(2-ureidoethyl)amino]-4-nitrobenzene, 4-[(2,3-dihydroxypropyl)amino]-3-nitro-1-trifluoro-methylbenzene, (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 2,4-dinitro-1-hydroxynaphthalene, 1,4-di-[(2,3-dihydroxypropyl)amino]-9,10-anthraquinone, 1,4-di-[(2-hydroxyethyl) amino]-9,10-anthraquinone (CI61545, Disperse Blue 23), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl)amino]-9,10-anthraquinone (HC Red-No. 8), 1,4-diamino-9,10-anthraquinone (CI61100, Disperse Violet No. 1), 1-amino-4-(methylamino)-9,10-anthraquinone (CI61105, Disperse Violet No. 4, Solvent Violet No. 12), N-(6-((3-chloro-4-(methylamino)phenyl)imino)-4-methyl-3-oxo-1,4-cyclohexadien-1-yl)urea (HC Red No. 9), 2-((4-(di-(2-hydroxyethyl)amino)phenyl)amino)-5-((2-hydroxyethyl)amino) -2,5-cyclohexadien-1,4-dione (HC Green No. 1), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis-(dicyanomethylidene)indane, di-[4-(diethyl-amino)phenyl][4-(ethylamino)naphthyl]carbenium chloride (CI42595; Basic Blue No. 7), di-[4-(dimethylamino) phenyl][4-(phenylamino)naphthyl]carbenium chloride (CI44045; Basic Blue No. 26), Basic Blue No. 77, 8-amino-2-bromo-5-hydroxy-4-imino-6-[(3-(trimethylammonio)-phenyl)amino]-1(4H)-naphthalenone chloride (CI56059; Basic Blue No. 99), tri-(4-amino-3-methylphenyl)carbenium chloride (CI42520; Basic Violet No. 2), di-(4-aminophenyl)(4-amino-3-methylphenyl)carbenium chloride (CI42510; Basic Violet No. 14), 1-[(4-aminophenyl)azo]-7-(trimethylammonio)-2-naphthol chloride (CI12250; Basic Brown No. 16), 3-[(4-amino-2,5-dimethoxyphenyl)azo]-N,N,N-trimethylbenzolaminium chloride (CI112605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI12251; Basic Brown No. 17), 2-((4-aminophenyl)azo)-1,3-dimethyl-1H-imidazol-3-ium chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)azo-1H-imidazol-3-ium chloride (Basic Red No. 51), 2-hydroxy-1-[(2-methoxyphenyl)azo]-7-(trimethylammonio)naphthalene chloride (CI12245; Basic Red No. 76), 3-methyl-1-phenyl-4-[(3-(trimethylammonio) phenyl) -azolpyrazol-5-one chloride (CI12719; Basic Yellow No. 57), 1-methyl-4-((methylphenyl-hydrazono)methyl)pyridinium methyl sulfate (Basic Yellow No. 87), 1-(2-morpholinium-propylamino)-4-hydroxy-9,10-anthraquinone methyl sulfate, 1-[(3-(dimethylpropylaminium)-propyl)amino]-4-(methylamino)-9,10-anthraquinone chloride, 1-[di-(2-hydroxyethyl)amino]-3-methyl-4-[(4-nitrophenyl)azo]benzene (CI11210, Disperse Red No. 17), 1-[di-(2-hydroxyethyl)-amino]-4-[(4-nitrophenyl)azo]benzene, (Disperse Black No. 9), 4-[(4-aminophenyl)azo]-1-[di-(2-hydroxyethyl)amino]-3-methylbenzene (HC Yellow No. 7) or 2,6-diamino-3-[(pyridin-3-yl)azo]-pyridine and 2-((4-(ethyl-(2-hydroxyethyl)amino)-2-methylphenyl)azo)-5-nitro-1,3-thiazole (CI111935; Disperse Blue No. 106).

A colorant of the present invention can further contain any additives that are known and conventional for such preparations, for example perfume oils, chelating agents, waxes, preservatives, thickeners, alginates, guar gum, hair conditioning substances, such as for example cationic polymers or lanolin derivatives, or anionic, nonionic, amphoteric, or cationic surface-active substances. The use of amphoteric or nonionic surface-active substances is preferable, for example betaine surfactants, propoinates, and glycinate, such as for example cocoamphoglycinates or cocoamphodiglycinates, ethoxylated surfactants with from 1 to 1000 ethylene oxide units, preferably with from 1 to 300 ethylene oxide units, such as for example glyceride alkoxylates, for example with 25 ethylene oxide units, ethoxylated castor oil, polyglycolamide, ethoxylated alcohols and ethoxylated fatty alcohols (fatty alcohol alkoxylates) and ethoxylated fatty acid sugar esters, especially ethoxylated sorbitan fatty acid ester. The aforementioned components are used in the conventional amounts for such purposes, for example the surface-active substances are used in a concentration of from 0.1 to 30 percent by weight, and the conditioning agents in an amount of from 0.1 to 5 percent by weight.

The colorant of the present invention, especially when used as a hair dye, can be used in the form of an aqueous or aqueous alcoholic solution, a creme, a gel, an emulsion, or an aerosol foam, where the hair dye can either be in the form of a single component preparation as well as in the form of a multiple component preparation, for example in the form of a two-component preparation, wherein the respective dye derivative of the generic formula (I) is packed separately from the other components, and the ready-to-use hair dye is prepared immediately before use by mixing the two components together.

A colorant of the present invention will exhibit a pH of from about 2 to 10, preferably from about 5 to 10, and especially a neutral to basic pH value of from about 7 to 10. Both organic as well as inorganic acids or bases are suitable for use in adjusting the pH value in the present invention.

The following can be named as suitable acids: α-Alpha-hydroxy carboxylic acids, such as for example glycolic acid, lactic acid, tartaric acid, citric acid or malic acid, ascorbic acid, gluconic acid lactone, acetic acid, hydrochloric acid, or phosphoric acid, as well as mixtures of these acids. Suitable bases that can be named in particular include sodium carbonate, sodium bicarbonate, alkanolamine, for example monoethanolamine or triethanolamine, ammonia, aminomethylpropanol and sodium hydroxide.

For using the colorant of the present invention, as a rule one takes a quantity that is sufficient for the coloring of hair, about 30 to 120 grams depending on the length of the hair, and applies this hair dye to the hair, then the hair coloring agent is allowed to react at from about 15 to 45° C. for from about 1 to 60 minutes, preferably from 5 to 30 minutes, and the hair is then thoroughly rinsed with water, washed with a shampoo if necessary, and finally dried.

Provided that no oxidizing agent has been added to the coloring preparation, the above-described colorant can further contain common natural or synthetic polymers as well as modified polymers obtained from natural sources that are used as cosmetic agents, whereby they can achieve a sealing of the hair at the same time that the hair is dyed. Such agents are generally referred to as tone sealers or color strengtheners.

Known synthetic polymers that can be used for this type of in cosmetics application that can be mentioned include, for example, polyvinylpyrrolidone, polyvinylacetate, polyvinylalcohol or polyacrylic compounds such as polyacrylic acid or polymethacrylate, basic polymerides of the esters of polyacrylic acid or polymethylacrylate with aminoalcohols, for example their salts or quaternization products, polyacrylonitrile, polyvinyl acetate as well as copolymerides of such compounds, such as for example polyvinylpyrrolidone-vinyl acetate; while examples of natural polymers or modified natural polymers would be chitosan (deacetylated chitin) or chitosan derivatives.

The aforementioned polymers can be contained in the colorant of the present invention in the usual amounts of such agents used for this purpose, particularly in an amount of from about 1 to 5 percent by weight. The pH value for the tone sealants or color sealants of the present invention is preferably from about 6 to 9.

The application of hair dyes with added sealants is effected in a known and conventional manner by moistening the hair with the sealant, setting the hair in a hairstyle, and then drying.

The colorant of the present invention enables a uniform, intense and durable coloring of keratin fibers (for example human hair, wool, or fur) without appreciable coloring of the skin and particularly of the skin of the head, this coloring being able to last through five or more hair washings without appreciable fading of the hair color.

The following examples will more clearly illustrate the object of the invention, without limiting it in any way.

EXAMPLES

Example 1

Preparation von 4-((E)-{4-[(2-bromoethyl)(ethyl)amino]phenyl}diazenyl)benzaldehyde 4 g of polymeric p-aminobenzaldehyde is suspended in a mixture of 80 mL of 2N hydrochloric acid and 40 mL of water, and this is cooled to 0°C. Next, 35 mL of a solution of 2.3 g of sodium nitrite in 8 mL of water is added dropwise over 30 minutes with further cooling to −3° C. To the brownish diazonium salt solution obtained in this way, 7.53 g of N-(2-bromoethyl)-N-ethylaniline is added portionwise (over 45 minutes) with continuous cooling. This is stirred with cooling for another 1 hour, at which time the preparation is poured onto ice. The reaction mixture is then slowly neutralized with 30% sodium hydroxide (ca. 40 mL), stirred at room temperature for 30 minutes, and the precipitate that formed is filtered off, washed with water, and dried under vacuum. The crude product is then chromatographed on silica gel with a mixture of heptane and ethyl acetate (1:2).

Yield: 5.75 g of an orange-red powder $^1$H-NMR (d$_6$-DMSO/300 MHz): δ=1.16 (t, 3H, methyl), 3.57 (q, 2H, methylene), 3.66-3.68 (m, 2H, methylene), 3.81-3.84 (m, 2H, methylene), 6.90 (d, 2H, J=9.3 Hz, phenyl), 7.84 (d, 2H, J=9.3 Hz, phenyl), 7.93 (d, 2H, J=8.4 Hz, phenyl), 8.05 (d, 2H, J=8.7 Hz, phenyl) 10.07 (s, 1H, formyl).

Example 2

Preparation of 3-(2-{ethyl-4-[(E)-(4-{(E)-[(2Z)-2-(3-methyl-1,3-benzothiazol-2(3H)ylidene)hydrazono]methyl}phenyl)diazenyl]anilino}ethyl)-1-methyl-1H-imidazol-3-ium bromide Step 1: Preparation of 4-((E)-{4-[(2-bromoethyl)(ethyl)amino]phenyl}diazenyl)benzaldehyde-((2Z)-3-methyl-1,3-benzothiazol-2(3H)ylidene) hydrazone A mixture of 0.2 g of 4-((E)-{4-[(2-bromoethyl)(ethyl)amino]phenyl}diazenyl)benzaldehyde and 0.13 g of N-methylbenzothiazolium hydrazone hydrochloride (MBTH) in 10% acetic acid is stirred at room temperature for 60 minutes. Next, the preparation is diluted with 50 mL of water and cooled with ice. The reaction mixture is made neutral with 2N sodium hydroxide, and the precipitate that formed is suction filtered off, washed with water, and product obtained is dried under vacuum.

Yield: 0.26 g of a red powder $^1$H-NMR (d$_6$-DMSO/300 MHz): δ=1.16 (t, 3H, methyl), 3.52 (q, 2H, methylene), 3.54 (s, 3H, methyl), 3.60-3.68 (m, 2H, methylene), 3.80-3.82 (m, 2H, methylene), 6.88 (d, 2H, J=9.3 Hz, phenyl), 7.11-7.13 (m, 1H, benzothiazole), 7.33-7.36 (m, 2H, benzothiazole), 7.63-7.66 (m, 1H, benzothiazole), 7.82 (d, 2H, J=9.0 Hz, phenyl), 7.86-7.91 (m, 4H, phenyl), 8.46 (s, 1H, olefin).

Step 2: Preparation of 3-(2-{ethyl-4-[(E)-(4-{(E)-[(2Z)-2-(3-methyl-1,3-benzothiazol-2(3H)ylidene)hydrazono]methyl}phenyl)diazenyl]anilino}ethyl)-1-methyl-1H-imidazol-3-ium bromide A mixture of 0.2 g of 4-((E)-{4-[(2-bromoethyl) (ethyl)amino]phenyl}diazenyl)benzaldehyde-((2Z)-3-methyl-1,3-benzothiazol-2(3H)ylidene) hydrazone and 0.96 g of dimethyl sulfate in 25 mL of acetonitrile is heated to reflux for 48 hours. After removal of the solvent and dilution with ethyl acetate, the product is extracted with water. The aqueous phase isolated in this way is evaporated, the residue is washed again with ethyl acetate, and then dried under vacuum.

Yield: 0.16 g of an orange-red powder

Melting point: 151° C.

Example 3

Preparation of 3-{2-[4-[(E)-(4-{(E)-[(2Z)-2-(3,4-dimethyl-1,3-thiazol-2(3H)ylidene)hydrazono]methyl}phenyl)diazenyl](ethyl)anilino]ethyl}-1-methyl-1H-imidazol-3-ium bromide Step 1: Preparation of 4-((E)-{4-[(2-bromoethyl)(ethyl)amino]phenyl}diazenyl)benzaldehyde-((2Z)-3,4-dimethyl-1,3-thiazol-2(3H)ylidene) hydrazone A mixture of 0.43 g of 4-((E)-{4-[(2-bromoethyl) (ethyl)amino]phenyl}diazenyl)benzaldehyde and 0.21 g of (2Z)-3,4-dimethyl-1,3-thiazol-2(3H)-one hydrazone hydrochloride in 10% acetic acid is stirred at room temperature for 60 minutes. Next, the preparation is diluted with 50 mL of water and cooled with ice. The reaction mixture is made neutral with 2N sodium hydroxide, then the precipitate that formed is suction filtered off, washed with water, and the product obtained is dried under vacuum.

Yield: 0.46 g of a garnet-red powder

1H-NMR (CDCl$_3$/300 MHz): δ=1.13 (t, 3H, methyl), 2.18 (s, 3H, methyl), 3.41 (q, 2H, methylene), 3.45 (s, 3H, methyl), 3.55-3.61 (m, 2H, methylene), 3.74-3.79 (m, 2H, methylene), 5.77 (s, 1H, thiazole), 6.78 (d, 2H, J=9.0 Hz, phenyl), 7.89-7.85 (m, 4H, phenyl), 7.91 (d, 2H, J=9.0 Hz, phenyl), 8.36 (s, 1H, olefin).

Step 2: Preparation of 3-{2-[4-[(E)-(4-{(E)-[(2Z)-2-(3,4-dimethyl-1,3-thiazol-2(3H)ylidene)hydrazono]methylyphenyl}diazenyl](ethyl)anilino]ethyl}-1-methyl-1H-imidazol-3-ium bromide A mixture of 0.25 g of 4-((E)-{4-[(2-bromoethyl)(ethyl)amino]phenyl}diazenyl)benzaldehyde-((2Z)-3,4-dimethyl-1,3-thiazol-2(3H)ylidene) hydrazone and 1.29 g of dimethyl sulfate in 30 mL of acetonitrile is heated to reflux for 48 hours. After removal of the solvent, the residue is diluted with ethyl acetate and the product is extracted with water. The aqueous phase isolated in this way is evaporated, the residue is washed again with ethyl acetate, and is dried under vacuum.

Yield: 0.18 g of a dark red powder

Melting point: 132° C.

Examples 4 and 5: hair dyes

| | |
|---|---|
| 2.5 mmol | Dye of the generic formula (I) according to Table 1 |
| 5.0 g | Ethanol |
| 4.0 g | Decyl polyglucose |
| 0.2 g | Ethylenediaminetetraacetic acid disodium salt hydrate |
| balance to 100.0 g | water, completely desalinated |

The dye solution is adjusted to a pH value of from 6 to 7. The hair coloring is carried out by applying a sufficient quantity of the colorant to the hair, and after an action period of 30 minutes at 40° C., the hair is rinsed with lukewarm water and then dried.

The coloring results are summarized in the following Table 1.

TABLE 1

| Example # | Dye of formula I (according to Example . . . ) | Coloring results |
|---|---|---|
| 4 | 3-(2-{Ethyl-4-[(E)-(4-{(E)-[(2Z)-2-(3-methyl-1,3-benzothiazol-2(3H)ylidene)hydrazono]methyl}phenyl)diazenyl]anilino}ethyl)-1-methyl-1H-imidazol-3-ium bromide (2) | Bright orange |
| 5 | 3-{2-[4-[(E)-(4-{(E)-[(2Z)-2-(3,4-Dimethyl-1,3-thiazol-2(3H)ylidene)hydrazono]methyl}phenyl)diazenyl](ethyl)anilino]ethyl}-1-methyl-1H-imidazol-3-ium bromide (3) | Wine red |

All percent figures represent percent by weight—unless otherwise indicated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cationic azo azine dye of the generic formula (I),

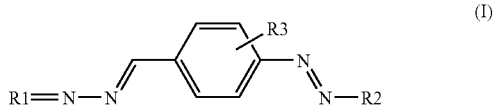

where

R1 is selected from residues having the formulas (II), (III), (IV), (V), and (VI),

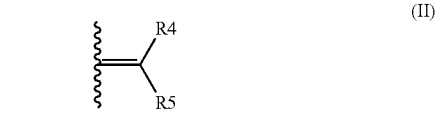

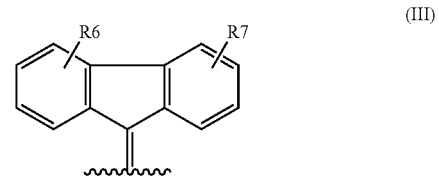

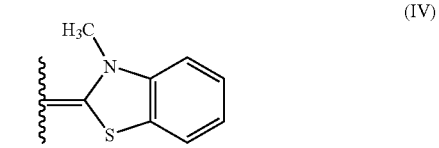

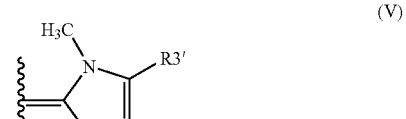

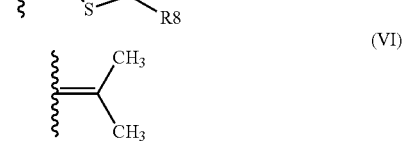

R2, R4, and R5 can be the same or different and independently from one another are selected from residues having the formulas (VII), (VIII), and (IX);

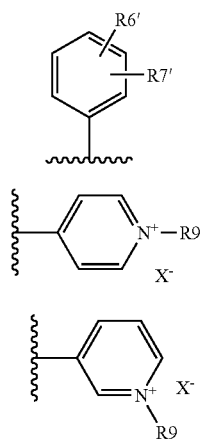

R3, R3', R6, R6', R7, R7', and R8 can be the same or different and independently from one another equal hydrogen, a $C_1$-$C_6$-alkylamine group, a $C_1$-$C_6$-N,N-dialkylamino group, a $C_1$-$C_6$-N,N-dihydroxyalkylamino group, a $C_1$-$C_6$-N-hydroxyalkyl-N-alkylamino group, a $C_1$-$C_6$-alkylcyano group, a nitro group, a cyano group, an amino group, a nitroso group, a hydroxyl group, a methoxymethyl group, a tert-butyl group, an iso-propyl group, a $C_1$-$C_6$-alkyl group, a $C_1$-$C_6$-alkyloxy group, a $C_1$-$C_6$-hydroxyalkyl group, a $C_1$-$C_6$-alkylcarboxylic acid group, a $C1$-$C_6$-alkylcarboxylic acid ester group, a $C_1$-$C_6$-alkylsulfonic acid group, a $C_1$-$C_6$-alkylsulfonic acid ester group, or an —N-(L)-$B^+$-group; L stands for a $C_1$-$C_6$ alkylene group and $B^+$ represents a) an aromatic, heterocyclic quaternary ammonium compound or b) a nonaromatic heterocyclic quaternary ammonium compound, or c) a quaternary alkylammonium compound or arylammonium compound of the formula $NR_aR_bR_c$, where $R_a$, $R_b$, and $R_c$ independently from one another indicate a benzyl residue, a phenyl residue or a $C_1$- to $C_6$-alkyl residue, an ethyl residue, a propyl residue, an isopropyl residue or a butyl residue, where the above-named alkyl residues can be unsubstituted or substituted with one or more hydroxyl groups or amino groups, or d) a quaternary phosphonium group; R9 equals a branched or linear $C_1$-$C_6$-alkyl group, a branched or linear $C_2$-$C_4$-hydroxyalkyl group or a branched or linear $C_4$-$C_6$-polyhydroxyalkyl group; and $X^-$ is an anion; provided that at least one of the residues R1, R2, and R3 contains at least one cationic group.

2. A cationic azo azine dye of formula (I) as recited in claim 1, wherein said dye is selected from the group consisting of 3-(2-{ethyl-4-[(E)-(4-{(E)-[(2Z)-2-(3-methyl-1,3-benzothiazol-2(3H)ylidene)hydrazono]methyl}phenyl)diazenyl]anilino}ethyl)-1-methyl-1H-imidazol-3-ium bromide, 3-{2-[4-[(E)-(4-{(E)-[(2Z)-2-(3,4-dimethyl-1,3-thiazol-2(3H)ylidene)hydrazono]methyl}phenyl)diazenyl](ethyl)anilino]ethyl}-1-methyl-1H-imidazol-3-ium bromide, 3-(2-{ethyl-4-[(E)-(4-{(E)-[(2Z)-2-(3,4,5-trimethyl-1,3thiazol-2(3H)ylidene)hydrazono]methyl}phenyl)diazenyl]anilino}ethyl)-1-methyl-1H-imidazol-3-ium bromide, 2-{ethyl-4-[(E)-(4-{(E)-[(2Z)-2-(3-methyl-1,3-benzothiazol-2(3H)ylidene)hydrazono]methyl}phenyl)diazenyl]anilino}-N,N,N-trimethylethanaminium bromide, 2-[4-[(E)-(4-{(E)-[(2Z)-2-(3,4-dimethyl-1,3-thiazol-2(3H)ylidene)hydrazono]methyl}phenyl)diazenyl](ethyl)anilino]-N,N,N-trimethylethanaminium bromide, 2-{ethyl-4-[(E)-(4-{(E)-[(2Z)-2-(3,4,5-trimethyl-1,3-thiazol-2(3H)ylidene)hydrazono]methyl}phenyl)diazenyl]anilino}-N,N,N-trimethylethanaminium bromide, 3-(2-{ethyl-4-[(E)-(4-{(E)-[(1-methyl-ethylidene)hydrazono]methyl}phenyl)diazenyl]anilino}ethyl)-1-methyl-1H-imidazol-3-ium bromide, 2-{ethyl-4-[(E)-(4-{(E)-[(1-methylethylidene)hydrazono]methyl}phenyl)-diazenyl]anilino}-N,N,N-trimethylethanaminium bromide, 3-{2-[4-[(E)-(4-{(E)-[(di-phenylmethylidene)hydrazono]methyl}phenyl)diazenyl](ethyl)anilino]ethyl}-1-methyl-1H-imidazol-3-ium methyl sulfate, 3-{2-[4-((E)-{4-[(E)-({bis-[4-(dimethylamino)-phenyl]methylidene}hydrazono)methyl]phenyl}diazenyl)(ethyl)anilino]ethyl}-1-methyl-1H-imidazol-3-ium bromide, 2-[4-((E)-{4-[(E)-({bis-[4-(dimethylamino)phenyl]methylidene}hydrazono)methyl]phenyl}diazenyl)(ethyl)anilino]-N,N,N-trimethylethanaminium bromide, 3-{2-[ethyl-4-((E)-{4-[(E)-(9H-fluoren-9-ylidenehydrazono)methyl]phenyl}diazenyl)anilino]ethyl}-1-methyl-1H-imidazol-3-ium, 2-[ethyl-4-((E)-{4-[(E)-(9H-fluoren-9-ylidenehydrazono)methyl]phenyl}diazenyl)anilino]-N,N,N-trimethylethanaminium bromide, 3-{2-[4-{(E)-[4-((E)-{[bis-(4-hydroxyphenyl)methylidene]hydrazono})methyl)-phenyl]diazenyl}(ethyl)anilino]ethyl}-1-methyl-1H-imidazol-3-ium bromide, 2-[4-{(E)-[4-((E)-{[bis-(4-hydroxyphenyl)methylidene]hydrazono}methyl)phenyl]diazenyl}(ethyl)-anilino]-N,N,N-trimethylethanaminium bromide, 3-{2-[4-{(E)-[4-((E)-{[bis-(4-nitro-phenyl)methylidene]hydrazono}methyl)phenyl]diazenyl}(ethyl)anilino]ethyl}-1-methyl-1H-imidazol-3-ium bromide, 2-[4-{(E)-[4-((E)-{[bis-(4-nitrophenyl)methylidene]hydrazono}methyl)phenyl]diazenyl}(ethyl)anilino]-N,N,N-trimethylethanaminium bromide, 4-[(Z)-[2E)-2-(4-{(E)-[4-(dimethylamino)phenyl]diazenyl}benzylidene)hydrazono]-(phenyl)methyl]-1-methylpyridinium methyl sulfate, 4-[(Z)-((2E)-2-{4-[(E)-(4-methoxy-phenyl) diazenyl]benzylidene}hydrazono)(phenyl)methyl]-1-methylpyridinium methyl sulfate, and 4-[(Z)-[(2E)-2-(4-{(E)-[4-(dimethylamino)phenyl]diazenyl}benzylidene)-hydrazono](4-hydroxyphenyl)methyl]-1-methylpyridinium methyl sulfate.

3. An agent for the coloring of keratin fibers, wherein said agent comprises at least one cationic azo azine dye of the generic formula (I) according to claim 1.

4. An agent as according to claim 3, wherein said agent comprises a cationic azo azine dye of the generic formula (I) in an amount of from 0.01 to 10 percent by weight.

5. An agent according to claim 3, wherein said agent comprises at least one further direct dye selected from the group consisting of nitro dyes, azo dyes, anthraquinone dyes, triphenylmethane dyes, and basic or acidic dyes.

6. An agent according to claim 3, wherein said agent comprises at least one common natural or synthetic polymer or at least one modified polymer from a natural source.

7. An agent according to claim 3, wherein said agent exhibits a pH value of from 2 to 11.

8. An agent according to claim 3, wherein said agent is a hair dye.

* * * * *